(12) United States Patent
Lambrecht et al.

(10) Patent No.: US 12,004,826 B2
(45) Date of Patent: Jun. 11, 2024

(54) DUAL BRAKE SETUP JOINT

(71) Applicant: INTUITIVE SURGICAL OPERATIONS, INC., Sunnyvale, CA (US)

(72) Inventors: Bram Gilbert Antoon Lambrecht, Redwood City, CA (US); Arjang M. Hourtash, San Francisco, CA (US); Saleh Tabandeh, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 870 days.

(21) Appl. No.: 17/043,550

(22) PCT Filed: Mar. 29, 2019

(86) PCT No.: PCT/US2019/024787
§ 371 (c)(1),
(2) Date: Sep. 29, 2020

(87) PCT Pub. No.: WO2019/191561
PCT Pub. Date: Oct. 3, 2019

(65) Prior Publication Data
US 2021/0015566 A1 Jan. 21, 2021

Related U.S. Application Data

(60) Provisional application No. 62/649,835, filed on Mar. 29, 2018.

(51) Int. Cl.
*A61B 34/30* (2016.01)
*A61B 34/35* (2016.01)
(Continued)

(52) U.S. Cl.
CPC .............. *A61B 34/30* (2016.02); *A61B 34/35* (2016.02); *B25J 19/0004* (2013.01); *A61B 2017/00973* (2013.01); *A61B 34/74* (2016.02)

(58) Field of Classification Search
CPC ......... A61B 34/30; A61B 34/35; A61B 34/74; A61B 2017/00973; A61B 2034/302;
(Continued)

(56) References Cited

U.S. PATENT DOCUMENTS 5,327,055 A 7/1994 Danielson et al.
5,497,057 A 3/1996 Danielson et al.
(Continued)

FOREIGN PATENT DOCUMENTS

DE 202016007293 U1 12/2016
EP 1905552 A1 4/2008
(Continued)

OTHER PUBLICATIONS

International Preliminary Report on Patentability and Written Opinion for Application No. PCT/US2019/024787, dated Oct. 8, 2020, 10 pages.
(Continued)

*Primary Examiner* — Victor L Macarthur
(74) *Attorney, Agent, or Firm* — Artegis Law Group, LLP

(57) ABSTRACT

A system, e.g., a computer-aided medical system, includes a first link, a second link, a joint, and a dual brake assembly. The first link has a first end portion and a second end portion. The second link has a first end portion and a second end portion. The joint is connected to the second end portion of the first link and to the first end portion of the second link. The dual brake assembly is coupled to the first link and to the second link. The dual brake assembly includes a first
(Continued)

brake and a second brake. Braking provided by the dual brake assembly reduces relative motion between the first and second links.

18 Claims, 8 Drawing Sheets

(51) Int. Cl.
*B25J 19/00* (2006.01)
*A61B 17/00* (2006.01)
*A61B 34/00* (2016.01)

(58) Field of Classification Search
CPC ... A61B 2090/508; A61B 90/50; A61B 34/70; B25J 19/0004; B25J 9/106; B25J 11/00; B25J 17/0241
See application file for complete search history.

(56) References Cited

U.S. PATENT DOCUMENTS

| | | |
|---|---|---|
| 8,620,473 B2 | 12/2013 | Diolaiti et al. |
| 8,903,546 B2 | 12/2014 | Diolaiti et al. |
| 9,084,623 B2 | 7/2015 | Gomez et al. |
| 9,586,323 B2 | 3/2017 | Diolaiti et al. |
| 10,661,453 B2 * | 5/2020 | Koenig ............... B25J 13/02 |
| 2015/0055760 A1 | 2/2015 | Barker et al. |
| 2016/0045271 A1 | 2/2016 | Mcgrogan et al. |
| 2017/0333144 A1 | 11/2017 | Ziaei et al. |
| 2018/0079090 A1 | 3/2018 | Koenig et al. |
| 2020/0306997 A1 * | 10/2020 | Koenig ............. A61B 1/00149 |

FOREIGN PATENT DOCUMENTS

| | | |
|---|---|---|
| WO | WO-2008037799 A1 | 4/2008 |
| WO | WO-2012110317 A2 | 8/2012 |
| WO | WO-2013071057 A1 | 5/2013 |
| WO | WO-2013071071 A1 | 5/2013 |
| WO | WO-2017144302 A1 | 8/2017 |
| WO | WO-2018000870 A1 | 1/2018 |

OTHER PUBLICATIONS

International Search Report and Written Opinion for Application No. PCT/US2019/024787, dated Aug. 7, 2019, 14 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP19776815.3 dated Apr. 14, 2021, 08 pages.

* cited by examiner

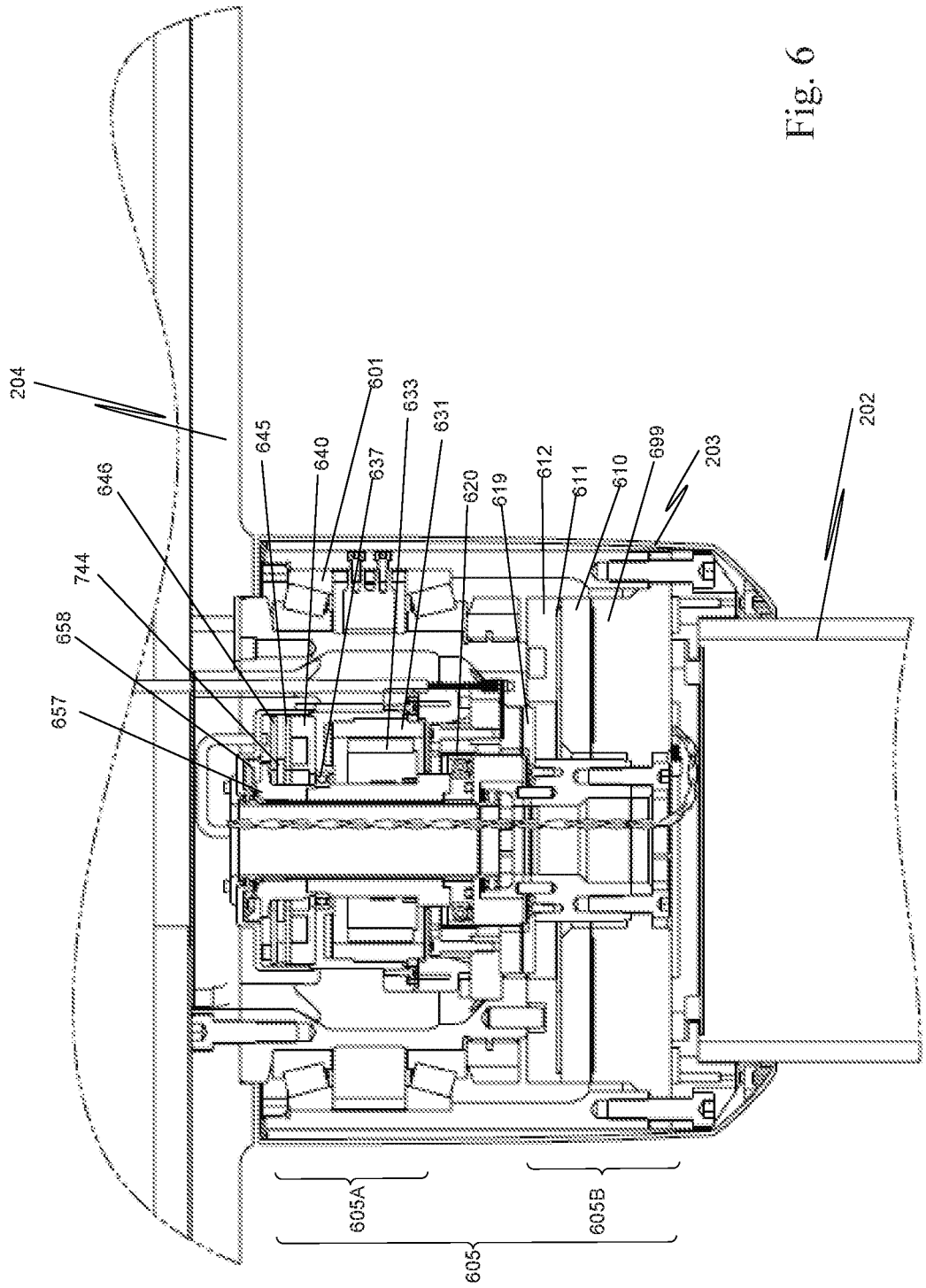

DUAL BRAKE SETUP JOINT

CROSS-REFERENCE TO RELATED APPLICATIONS

This application is a U.S. National Stage patent application of International Patent Application No. PCT/US2019/024787, filed on Mar. 29, 2019, the benefit of which is claimed, and claims priority to U.S. Provisional Application No. 62/649,835 filed Mar. 29, 2018, entitled "Dual Brake Setup Joint," each of which is incorporated herein by reference in its entirety.

BACKGROUND

Field of the Invention

The present invention relates generally to computer-aided medical systems, and more particularly to joint brakes of a computer-aided medical system.

Description of Related Art

Teleoperated system 100 is a computer-aided medical system (for example, a minimally invasive surgical system) that includes an endoscopic imaging system 192, a surgeon's console 194 (master), and a patient side support system 110 (slave), all interconnected by wired (electrical or optical) or wireless connections 196. One or more electronic data processors may be variously located in these main components to provide system functionality. Examples are disclosed in U.S. Pat. No. 9,060,678 B2.

Imaging system 192 performs image processing functions on, e.g., captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Console 194 also includes a stereoscopic video output display positioned such that images on the display are generally focused at a distance that corresponds to the surgeon's hands working behind/below the display screen. These aspects are discussed in U.S. Pat. No. 6,671,581.

Base 101 of patient side support system 110 supports an arm assembly that includes a passive setup arm assembly 120 and an actively controlled manipulator arm assembly 130. Actively controlled manipulator arm assembly 130 is referred to as entry guide manipulator 130.

In one example, setup arm assembly 120 includes two passive rotational setup joints 103 and 105. Rotational setup joints 103 and 105 allow manual positioning of coupled setup links 104 and 106 if the joint brakes for setup joints 103 and 105 are released. Alternatively, some of these setup joints may be actively controlled, and more or fewer setup joints may be used in various configurations. Setup joints 103 and 105 and setup links 104 and 106 allow a person to place entry guide manipulator 130 at various positions and orientations in Cartesian x, y, and z space. Specifically, setup joints 103 and 105 allow positioning in a (x, y) plane, and setup link 104 allows positioning in the z dimension. In particular, a prismatic setup joint (not shown) between setup link 104 of setup arm assembly 120 and base 101 may be used for vertical adjustments 112.

As shown in FIG. 1, a manipulator assembly yaw joint 111 is coupled between an end of setup link 106 and a first end, e.g., a proximal end, of a first manipulator link 113. Yaw joint 111 allows first manipulator link 113 to move with reference to setup link 106 in a motion that may be arbitrarily defined as "yaw" around a manipulator assembly yaw axis 123. As shown, the rotational axis of yaw joint 111 is aligned with remote center of motion 146, which is generally the position at which an instrument enters the patient (e.g., at the umbilicus for abdominal surgery).

In one embodiment, setup link 106 is rotatable in a horizontal or x, y plane and yaw joint 111 is configured to allow first manipulator link 113, sometimes referred to as link 113, in entry guide manipulator 130 to rotate about yaw axis 123. Setup link 106, yaw joint 111, and first manipulator link 113 provide a constantly vertical yaw axis 123 for entry guide manipulator 130, as illustrated by the vertical line through yaw joint 111 to remote center of motion 146.

A distal end of first manipulator link 113 is coupled to a proximal end of a second manipulator link 115, sometimes referred to as link 115, by a first actively controlled rotational joint 114. A distal end of second manipulator link 115 is coupled to a proximal end of a third manipulator link 117, sometimes referred to as link 117, by a second actively controlled rotational joint 116. A distal end of third manipulator link 117 is coupled to a distal portion of a fourth manipulator link 119, sometimes referred to as link 119, by a third actively controlled rotational joint 118.

In one embodiment, links 115, 117, and 119 are coupled together to act as a coupled motion mechanism. Coupled motion mechanisms are well known (e.g., such mechanisms are known as parallel motion linkages when input and output link motions are kept parallel to each other). For example, if rotational joint 114 is actively rotated, joints 116 and 118 are also actively rotated so that link 119 moves with a constant relationship to link 115. Therefore, it can be seen that the rotational axes of joints 114, 116, and 118 are parallel. When these axes are perpendicular to rotational yaw axis 123 of yaw joint 111, links 115, 117 and 119 move with reference to link 113 in a motion that may be arbitrarily defined as "pitch" around a manipulator assembly pitch axis.

The manipulator pitch axis extends into and out of the page in FIG. 1 at remote center of motion 146, in this aspect. The motion around the manipulator assembly pitch axis is represented by arrow 121. Since links 115, 117, and 119 move as a single assembly, first manipulator link 113 may be considered an active proximal manipulator link, and second through fourth manipulator links 115, 117, and 119 may be considered collectively an active distal manipulator link.

An entry guide manipulator assembly platform 132, sometimes referred to as platform 132, is coupled to a distal end of fourth manipulator link 119. An entry guide manipulator assembly 133 is rotatably mounted on platform 132. Entry guide manipulator assembly 133 includes an instrument manipulator positioning system.

Entry guide manipulator assembly 133 rotates plurality of instrument manipulator assemblies 140 as a group around axis 125. Specifically, entry guide manipulator assembly 133 rotates as a single unit with reference to platform 132 in a motion that may be arbitrarily defined as "roll" around an entry guide manipulator assembly roll axis 125, sometimes referred to as axis 125.

Each of a plurality of instrument manipulator assemblies 140 is coupled to entry guide manipulator assembly 133 by a different insertion assembly 135 (also called "insertion mechanism 135"). In one aspect, each insertion assembly 135 is a telescoping assembly that moves the corresponding instrument manipulator assembly away from and towards entry guide manipulator assembly 133. In FIG. 1, each of the insertion assemblies is in a fully retracted position.

Each of the plurality of instrument manipulator assemblies includes a plurality of motors that drive a plurality of outputs in an output interface of that instrument manipulator assembly. See U.S. Patent Application Publication No. US 2016/0184037 A1, for one example of an instrument manipulator assembly and a surgical instrument that can be coupled to the instrument manipulator assembly.

The joint brakes for rotational setup joints 103 and 105 are each a single brake that performs several functions. As discussed above during setup, the joint brakes for setup joints 103 and 105 are released to allow manual positioning of coupled setup links 104 and 106.

To help ensure that setup joints 103 and 105 don't move inadvertently in a fault condition, the joint brakes are power-off brakes, e.g., a brake that requires power to physically disengage in normal operation. To help ensure that the surgical tools can still be pushed out of the way to access the patient during an emergency, a maximum torque, referred to as an egress torque, that the single joint brake may apply is specified. Above this egress torque, the joint brake slips.

To reduce or minimize vibration of the end effector during a procedure (e.g., the cannula and the instrument tips), a stationary setup joint (e.g., setup joints 103 and 105) applies a force or torque opposing to the forces or torques required to accelerate and decelerate components (e.g., entry guide manipulator 130) physically coupled between the setup joint and the end effector. For a procedure performed using patient side support system 110, the required torque during a procedure at setup joints 103 and 105 is applied using the joint brake in each joint.

SUMMARY

A system, e.g., a computer-aided medical system, includes a first link, a second link, a joint, and a dual brake assembly. The first link has a first end portion and a second end portion. The second link has a first end portion and a second end portion. The joint is connected to the second end portion of the first link and to the first end portion of the second link. The dual brake assembly is coupled to the first link and to the second link The dual brake assembly includes a first brake and a second brake. Braking provided by the dual brake assembly reduces relative motion between the first and second links.

In one aspect, the first brake provides a first brake holding strength when physically engaged and the second brake provides a second brake holding strength when physically engaged. The second brake holding strength being different from the first brake holding strength, and in one aspect, the second brake holding strength is larger than the first brake holding strength.

In another aspect, the first brake is physically engaged when unpowered, and the second brake is physically disengaged when unpowered. The first brake is implemented as an actuator brake, and the second brake is implemented as a joint brake.

If the system is in a power off state, the first brake is unpowered and physically engaged and the second brake is unpowered and physically disengaged. If the system is in a fault state, a controller causes the first brake to be physically engaged and the second brake to be physically disengaged. If the system is in a clutch mode, the controller causes the first brake to be physically disengaged and the second brake to be physically disengaged. During a procedure, the controller causes the first brake to be physically disengaged and the second brake to be physically engaged.

In another aspect, the system includes an actuator and a controller. The actuator is coupled to the joint. Activation of the actuator causes the joint to move the second link relative to the first link. The controller is configured to cause the first brake to be physically engaged and the second brake to be physically engaged to restrict movement of the second link relative to the first link upon failure of the actuator in a state configured to cause movement of the second link relative to the first link.

In yet another aspect, the first brake and the second brake comprise a single brake. The system further includes an actuator having a housing and a shaft extending from the housing. The single brake is coupled to the actuator housing and to the shaft. In a first state, the single brake has a first holding strength and in a second state, the single brake has a second holding strength. The first holding strength is different from the second holding strength.

The single brake includes a brake rotor, a caliper and a variable load assembly. The brake rotor is mounted on the shaft. The caliper is coupled to the housing. The variable load assembly is coupled to the caliper. In a first state, the variable load assembly applies a first force on the caliper, and in a second state the variable load assembly applies a second force on the caliper. The first force is different from the second force.

In still another aspect, the controller is coupled to the first brake and to the second brake and the controller is configured to:

physically disengage the first brake and physically disengage the second brake to allow free movement of the second link relative to the first link; and physically engage the first brake and physically disengage the second brake to restrict movement of the second link relative to the first link; and physically disengage the first brake and physically engage the second brake during a procedure performed using the system; and physically engage the first brake and physically engage the second brake to restrict movement of the second link relative to the first link upon failure of an actuator in a state configured to cause movement of the second link relative to the first link.

A method of controlling motion of a second link relative to a first link in a system includes physically disengaging a first brake and physically disengaging a second brake to allow free movement of the second link relative to the first link, and physically engaging the first brake and physically disengaging the second brake to restrict movement of the second link relative to the first link. The method also includes physically disengaging the first brake and physically engaging the second brake during a procedure performed using the system, and physically engaging the first brake and physically engaging the second brake to restrict movement of the second link relative to the first link upon failure of an actuator in a state configured to cause movement of the second link relative to the first link.

A computer-aided medical system includes a patient side support system. The patient side support system includes a controller, a first link, a second link, and a joint assembly. The first link has a first end portion and a second end portion. The second link has a first end portion and a second end portion. The joint assembly is connected to the second end portion of the first link and to the first end portion of the second link.

The joint assembly includes an actuator and a dual brake assembly. The actuator is configured to cause the joint assembly to move the second link relative to the first link. The dual brake assembly is coupled to the first link, to the second link, and to the actuator. The dual brake assembly includes a first brake and a second brake.

The controller is coupled to the actuator and to the dual brake assembly. The controller is configured to command the dual brake assembly to reduce relative motion between the first and second links.

In this aspect, the first brake provides a first brake holding strength when physically engaged and the second brake provides a second brake holding strength when physically engaged. The second brake holding strength being different from the first brake holding strength, and in one aspect, the second brake holding strength is larger than the first brake holding strength.

Also, in this aspect, the first brake is physically engaged when unpowered, and the second brake is physically disengaged when unpowered. The first brake is implemented as an actuator brake, and the second brake is implemented as a joint brake.

If the computer-aided medical system is in a power off state, the first brake is unpowered and physically engaged and the second brake is unpowered and physically disengaged. If the computer-aided medical system is in a system fault state, the controller causes the first brake to be physically engaged and the second brake to be physically disengaged. If the computer-aided medical system is in a clutch mode, the controller causes the first brake to be physically disengaged and the second brake to be physically disengaged.

During a procedure, the controller causes the first brake to be physically disengaged and the second brake to be physically engaged. Alternatively, the second brake can also be engaged only during movements of distal components of the computer-aided medical system that produce a torque larger that torques that can be counteracted by the actuator. When the components of the computer-aided medical system are relatively stationary, or moving with torque less than torques that can be controlled by the actuator, the actuator at the joint is sufficient to counteract the torque required to accelerate the distal components, and so the second brake is physically disengaged.

BRIEF DESCRIPTION OF THE DRAWINGS

FIG. 6 is a cutaway drawing of one implementation of the shoulder joint assembly of FIG. 2.

Figure 1:
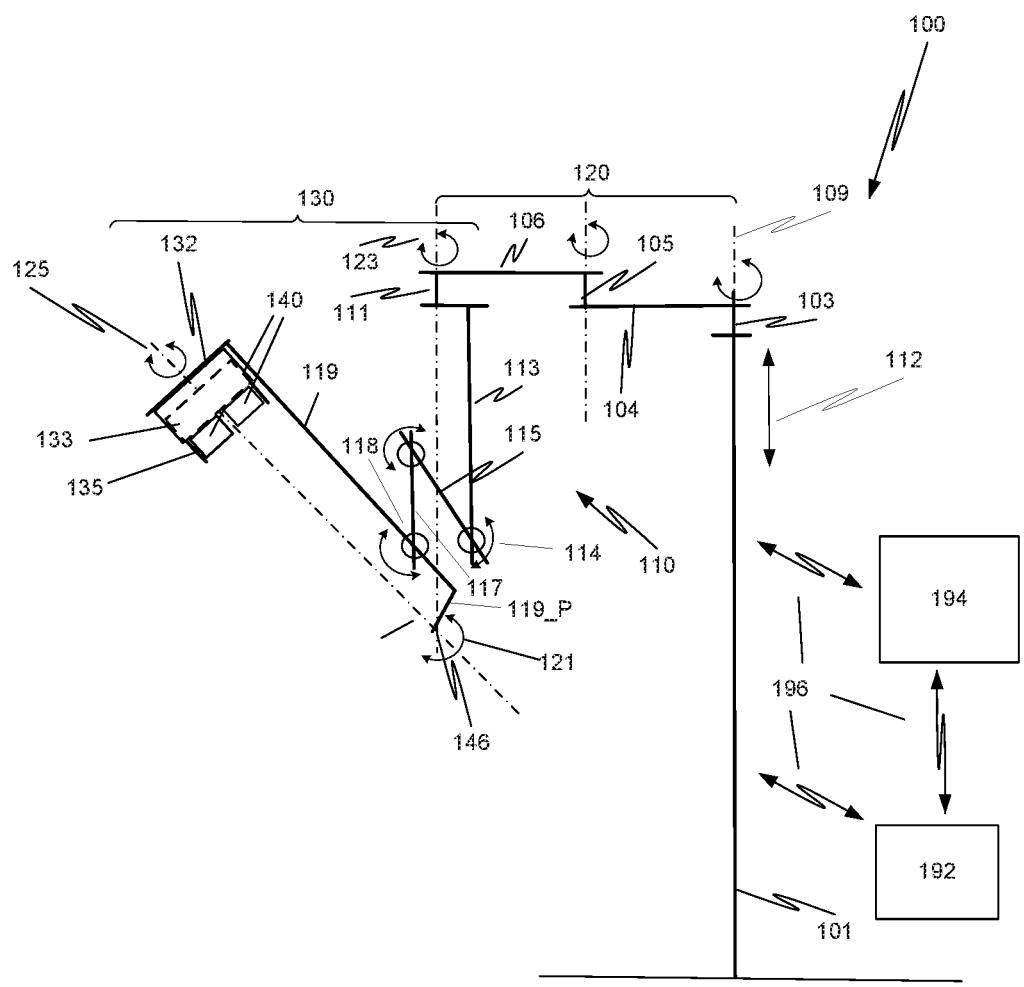
FIG. 1 is an illustration of a prior art computer-assisted teleoperated surgical system.

In the drawings, for single digit figure numbers, the first digit in the reference numeral of an element is the number of the figure in which that element first appears.

DETAILED DESCRIPTION

Figure 2:
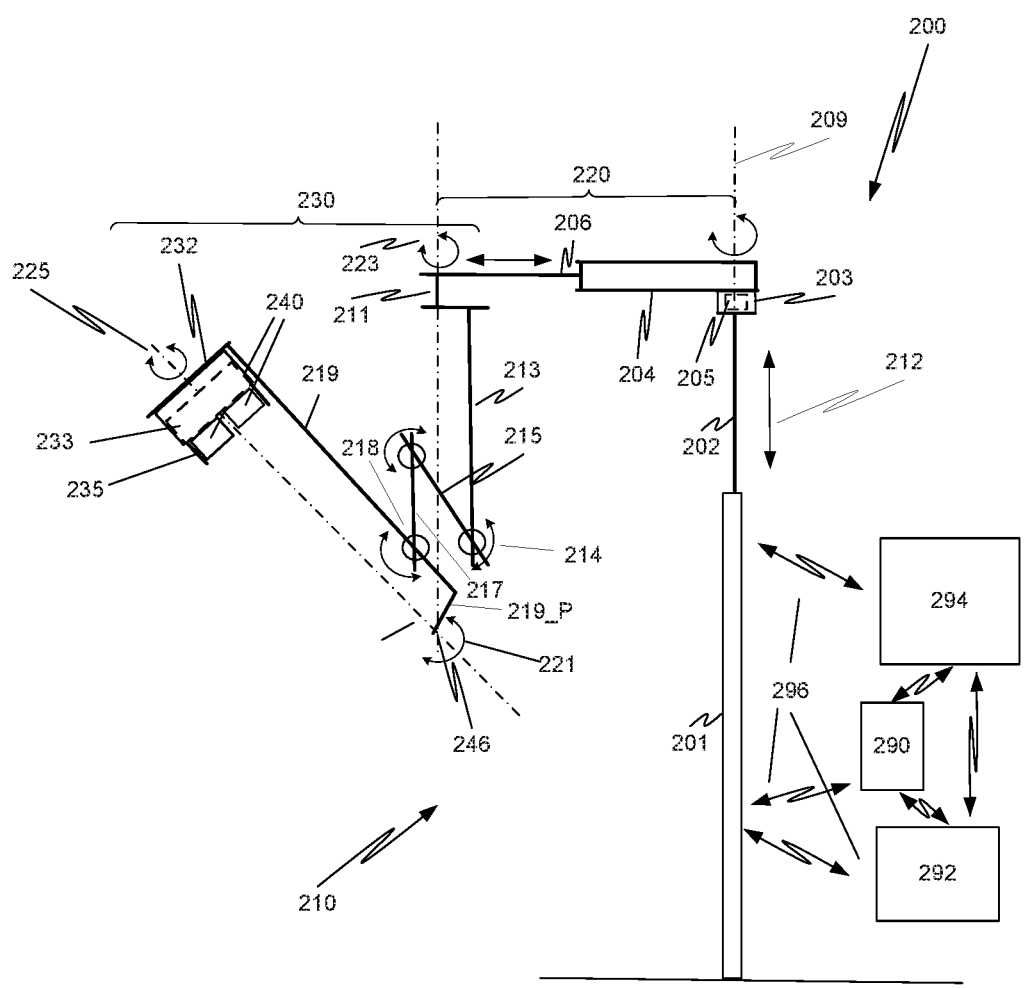
FIG. 2 is an illustration of a computer-aided medical system that includes a joint and a dual brake assembly.

Herein, a patient side support system 210 of a computer-aided medical system (FIG. 2) is first used as an example of a system that includes a dual 1 brake assembly that includes two portions. The first portion provides a first brake holding strength, when physically engaged, while the second portion provides a second brake holding strength, when physically engaged. In one aspect, the second brake holding strength is different from the first brake holding strength. In one aspect, the second brake holding strength is larger than the first brake holding strength. Herein, brake holding strength is sometimes referred to as holding strength. In various embodiments, the holding strength comprises one or more forces, torques (or moments), combination of forces or torques, etc. The use of patient side support system 210 is illustrative only and is not intended to limit use of the dual brake assembly to this one application. As described more completely below, the dual brake assembly can be utilized in a variety of systems.

In one aspect, joint assembly 203 in a patient side support system 210 includes a joint and a dual brake assembly 205. The joint rotatably couples first link 202 to second link 204. Dual brake assembly 205 provides the necessary braking functionality during all stages of operations of computer-aided medical system 200 without the compromises needed in the prior art systems with a single brake assembly associated with a joint. Sometimes, dual brake assembly 205 is referred to as brake assembly 205.

In one aspect, dual brake assembly 205 of joint assembly 203 includes two portions. The first portion provides a first brake holding strength, when physically engaged, while the second portion provides a second brake holding strength, when physically engaged. In one aspect, the second brake holding strength is different from the first brake holding strength. In one aspect, the second brake holding strength is larger than the first brake holding strength.

During a procedure performed with computer-aided medical system 200, in one aspect, the second portion of dual brake assembly 205 is engaged to prevent movement of second link 204 relative to first link 202. This restricts motion of yaw axis 223 of patient side support system 210 relative to a rotational axis 209 of joint assembly 203, which in turn minimizes vibration during the procedure. Rotational axis 209 of joint assembly 203 is parallel to yaw axis 223.

In the prior art system, with a single brake to achieve the necessary holding strength during a procedure, the egress torque was raised so that in some situations two average humans were required to apply the force required to make the single brake slip. (The number of required humans depended on their individual pushing power) The maximum holding strength of the brake during a procedure was still limited by requiring that users be able make the brake slip during an emergency. In contrast, the brake holding strength of the second portion of dual brake assembly 205 can be made as strong as necessary to dampen vibrations during a procedure, because dual brake assembly 205 decouples the requirements for a maximum holding strength during a procedure and for a user being able to make dual brake assembly 205 slip when needed.

For example, if computer-aided medical system 200 enters a fault state, controller 290 disengages the second portion of dual brake assembly 205 and engages the first portion of the dual brake assembly 205 in joint assembly 203. This releases the high brake holding strength of the second portion of dual brake assembly 205 and physically engages the smaller brake holding strength of the first portion of dual brake assembly 205. Engaging the first portion of dual brake assembly 205 in a fault state ensures that second link 204 does not move unintentionally, e.g., due to the effects of gravity. Fault states may be triggered by any number of environmental and operational parameters, including unexpected system operation, system movement that deviate from commanded movement, operator input or lack of input, interruption in power supply, emergency situations, etc. The holding strength of the first portion of the dual brake assembly 205 is such that second link 204 can be pushed out of the way in an emergency by a user so that a patient can be accessed.

As explained more completely below, in one aspect, when a master clutch activation is commanded, dual brake assembly 205 physically disengages all the braking capability in joint assembly 203 so that second link 204 can move freely relative to first link 202. In this aspect, first link 202 is proximal to second link 204, and so could be referred to as a proximal link. In this case, second link 204 would be a distal link. When the master clutch activation is dropped, the dual brake assembly engages the braking capability in joint assembly 203 to restrict motion of second link 204 relative to first link 202, e.g., the second portion of dual brake assembly 205 is physically engaged, in one aspect.

In another aspect, when the master clutch activation is dropped, all the braking capability of dual brake assembly 205 remains disengaged. The controller uses the actuator in joint assembly 203 to restrict motion of second link 204 relative to first link 202, until the actuator is insufficient or marginal to reduce vibration, e.g., when a command to move entry guide manipulator 230 is issued that requires a holding strength greater than can be supplied by the actuator, the controller issues a command to physically engage the second portion of dual brake assembly 205. Thus, in this aspect, dual brake assembly 205 is not engaged until dual brake assembly 205 is needed to control vibrations.

To help ensure that the joint in joint assembly 203 does not unintentionally move when power is off, the first portion of the dual brake assembly 205 is engaged so that motion of second link 204 relative to first link 202 is restricted. This helps to assure, for example, that during transportation (e.g., moving the system to another room or to another location in a room), the links in patient side support system 210 remain in the desired position.

The two portions of dual brake assembly 205 provide capabilities that were not previously available in a joint with a single brake due to the limitations on the holding strength of the single brake. As described previously, the brake holding strength of a single brake when engaged had to be such that application of the egress torque/force would cause the brake to slip. (Herein, egress torque/force means that if a rotational joint is used, a human or humans apply an egress force on a link distal to the rotational joint such that the egress torque is applied to the rotational joint, and if a prismatic joint is used, an egress force is applied to a link distal to the prismatic joint by one or more humans.) This limited the holding strength available to minimize vibrations during a procedure and the holding strength available to stop a condition in which a joint actuator failed in active state, e.g., a motor run-away condition.

For example, in teleoperated system 100, inertia of entry guide manipulator 130 is large due to its size, mass, and mechanical design, and so the torque required to accelerate entry guide manipulator 130 about yaw axis 123 must be sufficient to overcome the inertia of entry guide manipulator 130. Since yaw axis 123 and shoulder axis 109 are parallel, a torque at yaw axis 123 is reacted to by a similar magnitude torque at shoulder axis 109. For some moves of entry guide manipulator 130, the reaction load torque is large enough that the brake torque requirement for setup joint 103 would exceed the allowable egress torque, so a single unaided brake solution could not have an egress torque and also counteract torques on yaw axis 123 that could introduce vibrations.

The configuration of computer-aided medical system 200 is similar to that in teleoperated system 100 in that to accelerate entry guide manipulator 230 about yaw axis 223, a torque sufficient to overcome the inertia of entry guide manipulator 230 is required. Since yaw axis 223 and shoulder axis 209 are parallel, a torque at yaw axis 223 is reacted by a similar magnitude torque at shoulder axis 209. However, the two portions of dual brake assembly 205 allows dual brake assembly 205 to provide the required braking capability during a procedure to minimize vibrations, while at other times assuring that the torque required to move entry guide manipulator 230 does not exceed the egress torque. Similarly, dual brake assembly 205 is configured to counteract a condition in which a joint actuator fails in an active state. e.g., a motor runaway condition, so that motion of second link 204 relative to first link 202 is restricted. Thus, dual brake assembly 205 provides a range of capabilities that were not available in teleoperated system 100.

Prior to considering dual brake assembly 205 in further detail, computer-aided medical system 200 is described more completely. Patient side support system 210 is part of a computer-aided medical system that includes a controller 290, an operator's console 294, and an endoscopic imaging system 292. Controller 290, operator's console 294, and endoscopic imaging system 192 are interconnected to patient side support system 210 and to each other by wired (electrical or optical) or wireless connections.

A base 201 of patient side support system 210 supports an arm assembly that includes an actively controlled setup arm assembly 220 and an actively controlled manipulator arm assembly 230. Actively controlled manipulator arm assembly 230 is referred to as entry guide manipulator 230. Herein, actively controlled means that the device is under the control of a controller.

In this example, setup arm assembly 220 includes first link 202 (which is a first setup link in this example), a joint assembly 203, second link 204 (which is a second setup link in this example), and a third link 206 (which is a third setup link). A first prismatic joint (not visible) moves first link 202 into and out of base 201, i.e., moves first link 202 in first and second directions, to adjust the vertical height of second link 204 and third link 206 and thereby adjust the vertical height of entry guide manipulator 230. Joint assembly 203 (which in this example could also be referred to as a shoulder joint assembly or a rotational joint assembly) allows rotational positioning of coupled second link 204 and third link 206. A second prismatic joint (not visible) moves third link 206 into and out of second link 204, i.e., moves third link 206 in third and fourth directions, to adjust the horizontal position of entry guide manipulator 230.

The structure of entry guide manipulator 230 is similar to entry guide manipulator 130 described above. Specifically, the configuration and operation of links 213, 215, 217, 219, joints 214, 216, 218, platform 232, the entry guide manipulator assembly, the insertion assemblies, and plurality of instrument manipulator assemblies 240 of patient side support system 210 are the same as the configuration and operation of links 113, 115, 117, 119, joints 114, 116, 118, platform 132, entry guide manipulator assembly 133, insertion assemblies 135, and plurality of instrument manipulator assemblies 140 of patient side support system 110. Thus, the description of the configuration and operation of links 113, 115, 117, 119, joints 114, 116, 118, platform 132, entry guide manipulator assembly 133, insertion assemblies 135, and plurality of instrument manipulator assemblies 140 of patient side support system 110 is not repeated here for the configuration and operation of links 213, 215, 217, 219, platform 232, the entry guide manipulator assembly, the insertion assemblies, and plurality of instrument manipulator assemblies 240 of patient side support system 210.

Controller 290 is connected to each of the actively controlled joints in patient side support system 210, to actuators that control the operation of the insertion assemblies, and to plurality of instrument manipulator assemblies 240. Herein, when it is stated that controller 290 performs an act, it means that controller 290 issues a command or signal to a component that performs the act in response to the command or signal.

Herein, a single controller is referenced and described. Although described as a single controller, it is to be appreciated that this controller may be implemented in practice by any one of or any combination of hardware, software that is executed on a processor, and firmware. Also, a controller's functions, as described herein, may be performed by one unit or divided up among different components, each of which may be implemented in turn by any one of or any combination of hardware, software that is executed on a processor, and firmware. When divided up among different components, the components may be centralized in one location or distributed across the computer-aided medical system for distributed processing purposes.

A processor should be understood to include at least a logic unit and a memory associated with the logic unit. Thus, in various embodiments, a controller system includes programmed instructions (e.g., a non-transitory machine-readable medium storing the instructions) to implement some or all of the methods described in accordance with aspects disclosed herein. Any of a wide variety of centralized or distributed data processing architectures may be employed. Similarly, the programmed instructions may be implemented as a number of separate programs or subroutines, or they may be integrated into a number of other aspects of the systems described herein. In some embodiments, the controller system supports wireless communication protocols such as Bluetooth, Infrared Data Association (IrDA) protocol, Home Radio Frequency (HomeRF) protocol, IEEE 802.11 protocol, Digital Enhanced Cordless Telecommunications (DECT) protocol, and Wireless Telemetry protocol.

As described above, dual brake assembly 205 is included in a shoulder joint assembly, which includes a rotational joint. However, the novel dual brake assembly is not limited to use in rotational joints. The dual brake assembly can also be used, for example, with a prismatic joint.

Also, the dual brake assembly can be used in actively controlled joints and in passive joints. An actively controlled joint is a joint that includes an actuator (e.g., a motor) configured to move or assist motion of the actively controlled joint, and the actively controlled joint couples one link to another link. A controller uses the actuator to move one link relative to the other link. While a passive joint also couples one link to another link, a passive joint does not include an actuator configured to move the passive joint. Thus, to move a passive link, a user supplies the necessary torque/force.

Figure 3A:
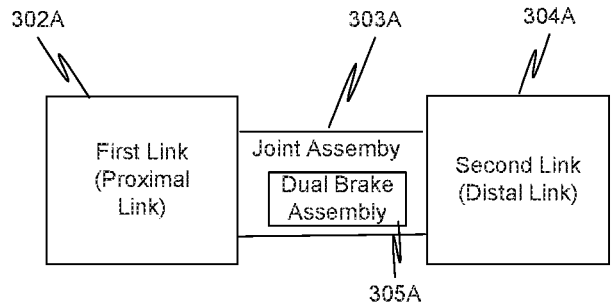
FIGS. 3A to 3E are schematic diagrams of different implementations of a portion of a system that includes a first link, a second link, and a joint assembly that includes a joint and a dual brake assembly.

In general, as illustrated in FIG. 3A, a system includes a first link 302A (e.g., a proximal link) having a first end portion and a second end portion and a second link 304A (e.g., a distal link) having a first end portion and a second end portion. A joint assembly 303A connects the second end portion of first link 302A and to the first end portion of second link 304A so that second link 304A can be moved relative to first link 302A. Use of a joint, prismatic or rotational, two couple two links in a system is known, and so is not described in further detail here.

Joint assembly 303A includes a dual brake assembly 305A. Dual brake assembly 305A is coupled to first link 302A and to second link 304A. Dual brake assembly 305A is actively controlled by a controller, such as controller 290.

While in this example, dual brake assembly 305A is included in joint assembly 303A, this is illustrative only and is not intended to be limiting. In general, dual brake assembly 305A includes two portions, a first portion that provides braking when dual brake assembly 305A is not powered, and a second portion that provides braking when dual brake assembly 305A is powered.

Above, dual brake assembly 205 is described as including two portions. The first portion provides a first brake holing strength, when physically engaged, while the second portion provides a second brake holding strength, when physically engaged. The second brake holding strength is different from the first brake holding strength, and in one aspect, the second brake holding strength is larger than the first brake holding strength. Similarly, each of the dual brake assemblies, described herein, includes similar two portions. In one aspect, the first portion is a first brake and the second portion is second brake. In all examples of the dual brake assembly including dual brake assembly 305A, the dual brake assembly reduces relative motion between the first and second links coupled to the dual brake assembly.

A controller is coupled to dual brake assembly 305A to control the states of the first brake and the second brake. In one aspect, if the system is in a fault state, the controller causes the first brake to be physically engaged and the second brake to be physically disengaged. If the system is in a clutch mode, the controller causes the first brake to be physically disengaged and the second brake to be physically disengaged. During a procedure, the controller causes the first brake to be physically disengaged and the second brake to be physically engaged.

Herein, when it is stated that a brake is engaged or is physically engaged, it means that the brake provides at least some braking. When it is stated that a brake is disengaged or is physically disengaged, it means that the brake does not provide braking.

Figure 3B:
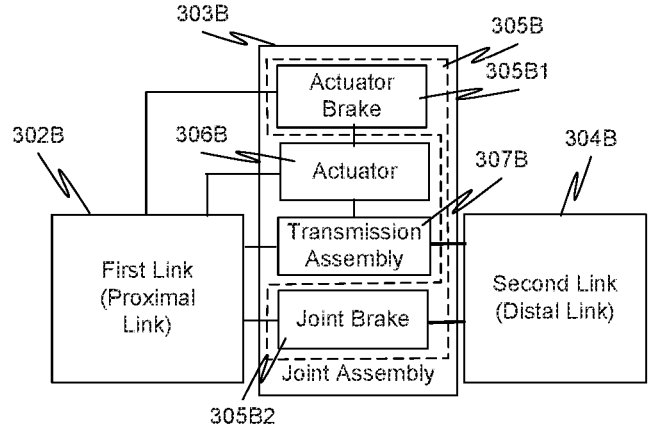
Figure 3C:
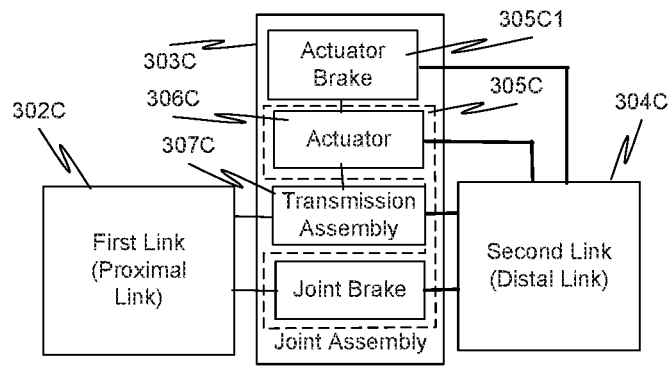
Figure 3D:
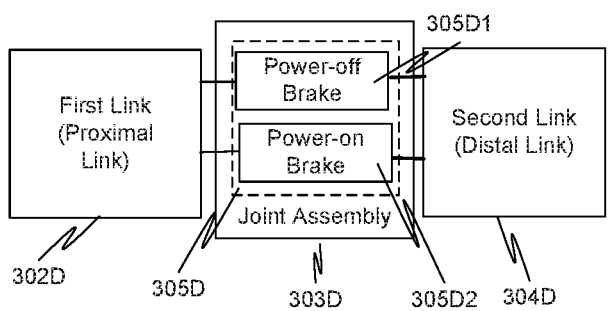
Figure 3E:
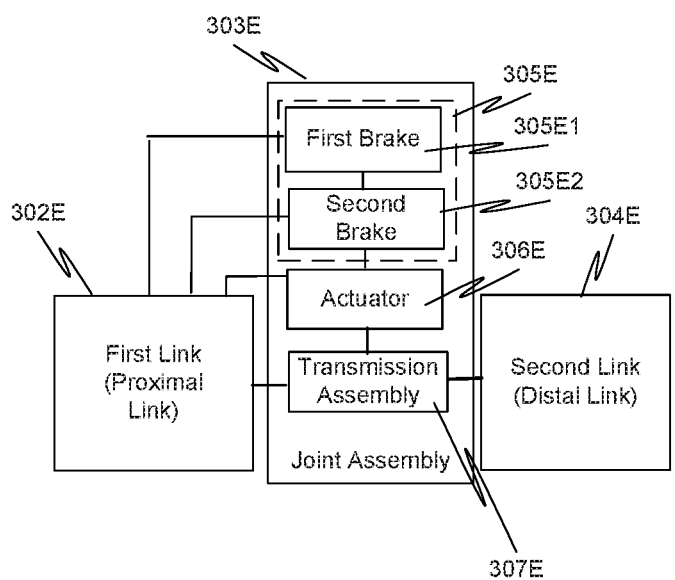

FIGS. 3B to 3E are schematic diagrams of possible implementations of joint assembly 303A and dual brake assembly 305A of FIG. 3A. FIGS. 3B, 3C, and 3E are configurations that include an actively controlled joint, while FIG. 3D is a configuration that includes a passive joint.

In FIG. 3B, a system includes a first link 302B (e.g., a proximal link) having a first end portion and a second end portion and a second link 304B (e.g., a distal link) having a first end portion and a second end portion. A joint assembly 303B connects the second end portion of first link 302B and to the first end portion of second link 304B so that second link 304B can be moved relative to first link 302B. Joint assembly 303B includes a joint and a dual brake assembly 305B. The joint is actively controlled by a controller. Dual brake assembly 305B is coupled to first link 302B and to second link 304B. In this example, dual brake assembly 305B is included in joint assembly 303B. However, this is illustrative only and is not intended to be limiting. Dual brake assembly 305B includes two portions, e.g., an actuator brake 305B1 (a first brake) and a joint brake 305B2 (a second brake).

In the example of FIG. 3B, joint assembly 303B also includes an actuator 306B and a transmission assembly 307B that are configured to move second link 304B relative to first link 302B. The output of actuator 306B is input to transmission assembly 307B. The output of transmission assembly 307B moves second link 304B.

Actuator 306B can be an electric motor, a pneumatic actuator, a hydraulic actuator, etc. Transmission assembly 307B reduces the output of actuator 306B to an output that is suitable for moving second link 304B relative to first link 302B. When actuator 306B is an electric motor, transmission assembly 307B can be, for example, a harmonic drive.

In FIG. 3B, the housings of actuator brake 305B1, actuator 306B, transmission assembly 307B, and joint brake 305B2 are stationary relative to first link 302B. Joint brake 305B2 is connected to second link 304B, while actuator brake 305B1 brakes the output of actuator 306B.

During a procedure performed using the system, in one aspect, joint brake 305B2 is physically engaged by a controller, and so provides braking. Actuator brake 305B1 is physically disengaged, and so does not provide braking.

In this aspect, joint brake 305B2 is configured to provide braking on second link 304B so that in response to reaction loads on second link 304B, second link 304B remains approximately stationary relative to first link 302B. Maintaining second link 304B approximately stationary during a procedure performed using the system minimizes vibration of any device, such as an instrument (e.g., a medical instrument such as a surgical instrument), coupled to the second end portion of second link 304B. Herein, approximately stationary means that any movement of second link relative to the first link does not cause the instrument coupled to second link 304B to move more than a predetermined acceptable amount. In one aspect the predetermined acceptable amount is one to three millimeters. Also, when stationary is used with respect to action of a brake on a link, it is understood that some small amount of movement of the link is acceptable so long as the small amount of movement does not result in the instrument moving more than the predetermined acceptable amount.

The braking provided by joint brake 305B2 during a procedure can be as large as necessary to restrict movement of second link 304B in response to reaction loads, without concern for being able to move second link 304B in a fault condition. In one aspect, joint brake 305B2 provides braking, e.g., is physically engaged, so long as a fault condition does not occur. In another aspect, the controller uses actuator 306B to restrict motion of second link 304B relative to first link 302B, until actuator 306B is insufficient or marginal to reduce vibration, e.g., when a command to move an assembly coupled to second link 304B is issued that requires a holding strength greater than can be supplied by actuator 306B, the controller issues a command to physically engage joint brake 305B2 of dual brake assembly 305B. Thus, in this aspect, joint brake 305B2 is not engaged until dual brake assembly 205 is needed to control vibrations.

If a fault condition occurs and if joint brake 305B2 is physically engaged, joint brake 305B2 is physically disengaged by the controller, and so provides no braking on joint assembly 303B. Thus, in a fault condition, joint brake 305B2 does not inhibit movement of second link 304B relative to first link 302B.

Actuator brake 305B1 is configured to restrict movement of second link 304B relative to first link 306B1 when power is off to dual brake assembly (e.g., the system is powered down) and in a fault condition. In one aspect, actuator brake 305B1 is a power-off brake, so that when power is removed from actuator brake 305B1, actuator brake 3025B1, (a first brake) provides braking on joint assembly 303B to restrict movement of second link 304B relative to first link 302B. However, the strength of actuator brake 305B1 is designed so that the braking allows the actuator brake 305B1 to slip in an emergency when sufficient force is applied to move second link 304B relative to first link 302B. In a fault condition, dual brake assembly 305B still provides braking, but allows movement of second link 304B relative to first link 302B if sufficient force is applied on second link 304B to cause actuator brake 305B1 to slip.

Recall that in this aspect during a procedure being performed using the system, joint brake 305B2 is physically engaged and actuator brake 305B1 is physically disengaged. If during the procedure, actuator 306B fails in an always on state, e.g., a motor run-away condition for an electric motor actuator, actuator brake 305B1 is physically engaged to counteract the actuator failure. In one aspect, a predetermined time after the always on fault is detected by the controller, the controller disengages joint brake 305B2. In another aspect, if during the procedure, actuator 306B fails in an always on state, e.g., a motor run-away condition for an electric motor actuator, actuator brake 305B1 is physically engaged to counteract the actuator failure and joint brake 305B2 is physically disengaged without any time delay.

Since actuator brake 305B1 acts directly on the output of actuator 306B, actuator brake 305B1 can have higher backlash, and lower torque relative to joint brake 305B2 and still control any reaction loads on second link 304B. This is because transmission assembly 307B reduces the effect of the wider tolerances. For example, transmission assembly 307B reduces the amount of backlash by the output reduction of ratio of transmission assembly 207B. For example if the backlash is six degrees and the reduction ratio is 120:1, the backlash at the output of transmission assembly 307B is 0.05 degrees. For example, transmission assembly 307B increases the torque by the output reduction of ratio of transmission assembly 307B. For example if the brake holding strength is one Newton-meter and the reduction ratio is 120:1, the holding strength at the output of transmission assembly 307B is 120 Newton-meters.

In a computer-aided medical system, the acceptable backlash is determined by determining the amount of movement of the attached instrument due to backlash, and so long as the movement is less than the predetermined acceptable amount. Any backlash that results in the instrument moving less than the predetermined acceptable amount is referred to as low backlash. Backlash is the amount a joint moves with very little load or torque applied. Stiffness determines the amount the joint deflects when more load is applied. For example, an applied force F might cause a joint to deflect an amount x. If the deflection is linear with respect to force, then the stiffness of the joint is k, where k=F/x. In the example of joint assembly 203, joint assembly 203 may deflect some small angle due to a torque required to overcome the inertia of entry guide manipulator 230. The higher the stiffness of dual brake assembly 205, the lower the deflection of joint assembly 203. The lower the deflection of joint assembly 203, the lower the amplitude of the vibration at the instrument tips. If the torque is reversing directions, then the total deflection is the sum of the backlash and the deflection due to the compliance (i.e., the inverse of the stiffness) of dual brake assembly 205.

In another aspect, during a procedure, joint brake 305B2 is physically engaged and actuator brake 305B1 is physically engaged. This has two advantages. First, with both brakes engaged, a larger reaction force can be counteracted on second link 304B. Alternatively, it may allow a smaller cheaper brake to be used as joint brake 305B2, because joint brake 305B2 does not need to be configured to counteract the largest anticipated reaction torque/force alone. The second advantage is that if the actuator should fail in an always on state, actuator brake 305B1 is already engaged. Of course, the disadvantage is that actuator 306B cannot be used to move second link 304B during the procedure.

In FIG. 3C, a system includes a first link 302C (e.g., a proximal link) having a first end portion and a second end portion and a second link 304C (e.g., a distal link) having a first end portion and a second end portion. A joint assembly 303C connects the second end portion of first link 302C and to the first end portion of second link 304C so that second link 304C can be moved relative to first link 302C. Joint assembly 303C includes a joint and a dual brake assembly 305C. The joint is actively controlled by a controller. Dual brake assembly 305C is coupled to first link 302C and to second link 304C. In this example, dual brake assembly 305C is included in joint assembly 303C. However, this is illustrative only and is not intended to be limiting. Dual brake assembly 305C includes two portions, e.g., an actuator brake 305C1 (a first brake) and a joint brake 305C2 (a second brake).

In the example of FIG. 3C, joint assembly 303C also includes an actuator 306C and a transmission assembly 307C that are configured to move second link 304C relative to first link 302C. The output of actuator 306C is input to transmission assembly 307C. The output of transmission assembly 307C moves second link 304C.

Actuator 306C can be an electric motor, a pneumatic actuator, a hydraulic actuator, etc. Transmission assembly 307C reduces the output of actuator 306C to an output that is suitable for moving second link 304C relative to first link 302C. When actuator 306C is an electric motor, transmission assembly 307C can be, for example, a harmonic drive.

In FIG. 3C, the housings of actuator brake 305C1, actuator 306C, transmission assembly 307C, and joint brake 305C2 are stationary relative to second link 304C. Joint brake 305C2 is connected to second link 304C, while actuator brake 305C1 brakes the output of actuator 306C. The operation of the components of joint assembly 303C is the same as the corresponding components of joint assembly 303B, and so is not repeated.

FIG. 3D is a schematic illustration of a passive joint assembly 303D, which does not include an actuator. In FIG. 3D, a system includes a first link 302D (e.g., a proximal link) having a first end portion and a second end portion and a second link 304D (e.g., a distal link) having a first end portion and a second end portion. Joint assembly 303D connects the second end portion of first link 302D and to the first end portion of second link 304D so that second link 304D can be moved relative to first link 302D. Joint assembly 303D includes a passive joint (an actuator is not used to move the joint) and dual brake assembly 305D. Dual brake assembly is actively controlled by a controller, such as controller 290, while the passive joint is not controlled by a controller.

Dual brake assembly 305D is coupled to first link 302D and to second link 304D. In this example, dual brake assembly 305D is included in joint assembly 303D. However, this is illustrative only and is not intended to be limiting.

Dual brake assembly 305D includes a power-off brake 305D1 (a first brake or a first portion) and a power-on brake 305D2 (a second brake or a second portion). Power-off brake 305D1 is physically engaged, when power is removed from dual brake assembly 305D, and is physically disengaged when power is supplied to dual brake assembly 305D. Power-on brake 305D2 is physically engaged, when power is applied to dual brake assembly 305D, and is physically disengaged, when power is removed from dual brake assembly 305D.

In this aspect, power-on brake 305D2 is configured to provide braking on second link 304D to restrict movement of second link 304D relative to first link 302D in response to reaction loads on second link 304D. Maintaining second link 304D approximately stationary during a procedure using the system minimizes vibration of any device, such as an instrument (e.g., a medical instrument such as a surgical instrument), coupled to the second end portion of second link 304D.

The braking provided by power-on brake 305D2 during a procedure can be as large as necessary to hold second link 304D in place in response to reaction loads, without concern for being able to move second link 304D if a fault condition occurs. Power-on brake 305D2 provides braking, e.g., is physically engaged, so long as a fault condition does not occur. If a fault condition occurs, power-on brake 305D2 is physically disengaged by the controller, and so provides no braking on second link 204B. Thus, when a fault occurs, power-on brake 305D2 does not inhibit movement of second link 304D relative to first link 302D.

Power-off brake 305D1 is configured to restrict movement of second link 304D relative to first link 306D when power is off to the system, when power is off to dual brake assembly 305D, and when a fault condition in the system occurs. The holding strength of power-off brake 305D1 is designed so that the braking allows power-off brake 305D1 to slip when sufficient torque/force is applied to move second link 304D relative to first link 302D. Thus, in a fault condition, dual brake assembly 305D still provides braking, but allows movement of second link 304D relative to first link 302D if sufficient torque/force is applied on second link 304D to cause power-off brake 305D1 to slip.

In FIG. 3E, a system includes a first link 302E (e.g., a proximal link) having a first end portion and a second end portion and a second link 304E (e.g., a distal link) having a first end portion and a second end portion. A joint assembly 303E connects the second end portion of first link 302E and to the first end portion of second link 304E so that second link 304E can be moved relative to first link 302E. Joint assembly 303E includes a joint and a dual brake assembly 305E. The joint is actively controlled by a controller. Dual brake assembly 305E is coupled to first link 302E and to second link 304E. In this example, dual brake assembly 305E is included in joint assembly 303E. However, this is illustrative only and is not intended to be limiting. Dual brake assembly 305E includes two portions, e.g., a first brake 305E1 and a second brake 305E2.

In the example of FIG. 3E, joint assembly 303E also includes an actuator 306E and a transmission assembly 307E that are configured to move second link 304E relative to first link 302E. The output of actuator 306E is input to transmission assembly 307E. The output of transmission assembly 307E moves second link 304E.

Actuator 306E can be an electric motor, a pneumatic actuator, a hydraulic actuator, etc. Transmission assembly 307E reduces the output of actuator 306E to an output that is suitable for moving second link 304E relative to first link 302E. When actuator 306E is an electric motor, transmission assembly 307E can be, for example, a harmonic drive.

In FIG. 3E, the housings of first brake 305E1, actuator 306E, transmission assembly 307E, and second brake 305E2 are stationary relative to first link 302E. Second brake 305E2 and first brake 305E1 both act directly on the output of actuator 306E. The operation of the components of joint assembly 303E is the same as the corresponding components of joint assembly 303B, and so is not repeated. Specifically, even though both second brake 305E2 and first brake 305E1 act on the output of actuator 306E, second brake 305E2 has a larger holding strength (suitable for handling reaction loads) than the holding strength of first brake 305E1 (holding strength limited by egress torque/force needed to make brake slip).

In one aspect, each of the joint brakes and the power-on brake are brakes for rotational joints, and are implemented, for example, using a stationary electromagnet. A brake rotor is attached to flexure, which is then connected a shaft connected to the second link. When electrical power is applied to an electromagnet coil a magnetic field is created. The magnetic force is strong enough to deflect the flexure and pull the brake rotor across a small air gap into a face of the electromagnet. The friction connection between the face of the electromagnet and brake rotor provides a braking force on the shaft. Increasing the current through the electromagnet increases the holding power of the brake. When power is removed from the electromagnet, the flexure pulls the armature across the air gap and away from the face of the electromagnet. With an air gap between the electromagnet and the armature, the shaft of the joint is free to rotate without any residual drag. Alternatively, any electro-mechanical power-on brake could be used so long that brake has the brake holding strength required.

In one aspect, each of the joint brakes acts directly on its joint without an intermediate transmission assembly. This configuration has the advantage that additional compliance from the transmission assembly is eliminated. However, since the torque multiplication factor associated with the transmission assembly is lost, the joint brake is physically larger and heavier (relative to the joint brake that acts through a transmission assembly) so that the joint brake itself can produce the required holding strength.

In one aspect, each of the actuator brakes and each of the power-off brakes is implemented, for example, using a permanent magnet that normally pulls a brake rotor towards a friction surface. The brake rotor is connected to a shaft that is connected to the second link. Friction between the friction surface and the brake rotor stops rotation of the shaft. When power is applied to the brake, a field of an electromagnet cancels the field of the permanent magnet and the rotor is free to move. Reversing the field of the electromagnet strengthens the magnetic to hold the rotor with more torque than the permanent magnet alone. Alternatively, any electro-mechanical power-off brake could be used so long that brake has the brake holding strength required. In another aspect, the brakes are spring-applied brakes, similar to the brake illustrated in FIGS. 5A and 5B, but without the variable spring force.

Figure 4A:
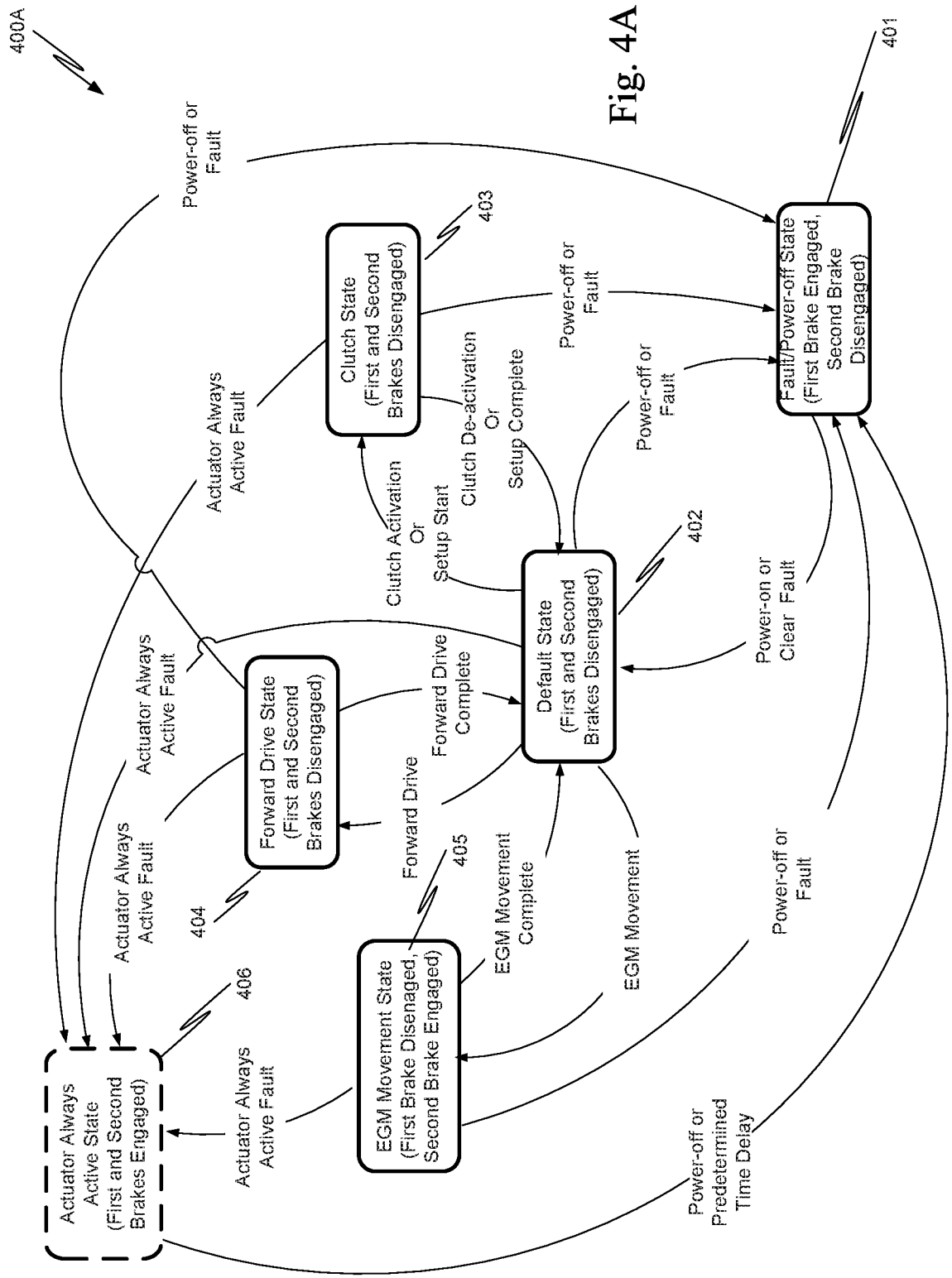
FIG. 4A is a first state diagram of a controller used to control the states of a dual brake assembly.

In one aspect, FIG. 4A is a representative state-diagram for a controller that controls each of the dual brake assemblies described above when implemented in joint assembly 203 of computer-aided medical system 200. In this aspect, joint assembly 203 is an actively controlled joint assembly. While the states are described as being states of controller 290, the states also are associated with states of dual brake assembly 205. Also, while the states are described with respect to a computer-aided system, this is illustrative only and is not intended to be limiting. The states of the dual brake assembly can be implemented in a wide variety of systems.

Controller 290 also can be implemented, as described above. In this example, the first brake of dual brake assembly 205 is physically engaged and provides braking whenever power is off to patient side support system 210 or when power is off to dual brake assembly 205. The brake holding strength of the first brake restricts motion of second link 204 relative to first link 202, but the brake holding strength is such that a user can apply an egress force on second link 204, which produces an egress torque that causes the first brake to slip and so second link 204 can be moved. When engaged, the brake holding strength of the second brake restricts movement of second link 204 relative to first link 202 during a procedure for reaction torques acting on the second link 204.

If a joint actuator fails in an always on state, controller 290 detects an actuator always active fault. Also, a fault may occur, power may be turned off to the computer-aided medical system, or power may be turned off to dual brake assembly 205. If an emergency or a fault event occurs, it may be necessary to manually remove instruments from a patient. In such a case, a user must be able to manually move the various links in the computer-aided medical system. If power fails for whatever reason, dual brake assembly 205 maintains the position of second link 204 relative to first link 202 so that motion due to gravity or some other force does not cause any unintended motion. State diagram 400A of controller 290 accounts for each of these events.

In a first state 401 (a fault/power-off state), the first brake is physically engaged and provides braking to joint assembly 203 that is associated with dual brake assembly 205. The second brake is physically disengaged and provides no braking to joint assembly 203. If computer-aided medical system 200 is powered off, controller 290 is shut down. In first state 401, the brake holding strength of the first brake restricts movement of second link 204 relative to first link 202, but the brake holding strength is such that a user or users can apply an egress force on second link 204, which produces an egress torque that in turn causes the first brake to slip, and so second link 204 can be moved.

When either power is turned-on or a fault is cleared, controller 290 enters second state 402, e.g., the system transitions from first state 401 to second state 402. In this example, second state 402 is default state. The default state is the state to which the system is switched before use. In this example, with first and second brakes and an actuator that can supply torque, there are three elements with each element having two possible states—physically engaged or physically disengaged. Thus, there are $2^3$, i.e., eight, possible states that could be selected as the default state. The possible states are presented in Table 1.

TABLE 1

| Default State | Actuator Providing Torque/Force | Actuator Neutral or Off | First Brake Engaged | First Brake Disengaged | Second Brake Engaged | Second Brake Disengaged |
|---|---|---|---|---|---|---|
| D1 | x |   |   | x |   | x |
| D2 | x |   | x |   |   | x |
| D3 | x |   |   | x | x |   |
| D4 | x |   | x |   | x |   |
| D5 |   | x |   | x | x |   |
| D6 |   | x | x |   |   | x |
| D7 |   | x | x |   | x |   |
| D8 |   | x |   | x |   | x |

One of these eight possible default states, state D8, has all three elements physically disengaged. State D8 is not considered, in this example, for the default state, because in state D8, it is not possible to hold a distal link in any specific position. With the elimination of state D8 as a default state, there are seven possible states that could be used as the default state depending on the configuration and use of the medical system. Thus, in this aspect, any of states D1 to D7 could be selected as the default state so long as the selected default state is consistent with the configuration and use of the medical system.

As an example, state D1 is selected as the default state. This is illustrative only and is not intended to be limiting. As just explained, consistent with the configuration and use of the medical system, any one of the first seven states in Table 1 could be selected as the default state.

Returning to FIG. 4A, in second state 402 (a default state in this example), controller 290 configures dual brake assembly 205 so that the first and second brakes are physically disengaged. Thus, in second state 402, the first and second brakes provide no braking to joint assembly 203. Controller 290 commands the actuator in joint assembly 203 to restrict movement of second link 204 relative to first link 202 for reaction torques on second link 204, while in second state 402. Thus, second state 402, in this aspect, is default state D1.

From second state 402, controller 290 can transition to several different states. States of interest with respect to joint assembly 203 include a third state 403 (a clutch state), a fourth state 404 (a forward drive state), and a fifth state 405 (an entry guide manipulator (EGM) movement state). Controller 290 remains in second state 402 until an event occurs, which causes controller 290 to transition to another state, i.e., one of states 401, 403, 404, 405, and 406. If while in second state 402, a power-off event or a fault event occurs, controller 290 transitions from second state 402 to first state 401. If the fault event is an actuator always active fault, controller 290 does not transition to first state 401, but instead transitions to a sixth state 406 (an actuator always active state).

Sixth state 406 is shown with a dotted line in FIG. 4A, because sixth state 406 is optional. See FIG. 4B. Sixth state 406 would typically not be used in normal operation, because the physical engagement of the first brake nullifies the operation of the actuator. Also, if in fault conditions, power is turned-off to the brakes and actuators, it would not be possible to implement sixth state 406 in response to a fault, because sixth state 406 assumes that power is available to the brakes and the actuators.

A user may issue a clutch command, which indicates a clutch activation. A user issues the clutch command to be able to freely move the links of computer-aided medical system 200. Alternatively, if the power is being turned on for the first time (a power-on event), a system setup is typically performed, in which the links are moved into position to allow sterile draping of all or part of computer-aided medical system 200. Thus, controller 290 transitions from second state 402 to third state 403 (which in this example is a clutch state), when either a clutch activation event or a set-up start event occurs.

In third state 403, controller 290 does not change the configuration of dual brake assembly 205, and so the first and second brakes remain disengaged. The actuator of joint assembly 203 is in a neutral state (motion of the joint is neither aided nor restricted by the actuator) and/or compensating for friction to allow motion of the joint in joint assembly 203.

If while in third state 403, a power-off event or a fault event occurs, controller 290 transitions from third state 403 to a first state 401, which in this example is a fault/power-off state. If the fault event is an actuator always active fault, controller 290 does not transition to first state 401, but instead transitions to a sixth state 406. If while in third state 403, a clutch-deactivation event or a setup complete event is received by controller 290, controller 290 transitions from third state 403 to second state 402.

If while in second state 402, controller 290 receives a forward drive event, controller 290 transitions from second state 402 to a fourth state 404, which in this example is a forward drive state. A forward drive event results from either a command generated by the controller in response to a specified condition (e.g., automatically configuring the EGM for draping or automatically configuring the EGM for transport) or in response to a user command, (e.g., from voice input, gesture input, physical input received at one or more pedals, buttons, touchscreens, or at one or more master input devices at the operator's console). In fourth state 404, both the first and second brakes of dual brake assembly 205 remain disengaged, and controller 290 commands the actuator in joint assembly 203 to follow a position trajectory.

If while in fourth state 404, a power-off event or a fault event occurs, controller 290 transitions from fourth state 404 to first state 401 (fault/power-off state). If the fault event is an actuator always active fault, controller 290 does not transition to first state 401, but instead transitions to a sixth state 406. If while in fourth state 404, a forward drive complete event is received by controller 290, controller 290 transitions from fourth state 404 to second state 402.

If while in second state 402, controller 290 receives an entry guide manipulator (EGM) movement event, controller 290 transitions from second state 402 to a fifth state 405, which is this example is an EGM movement state. An entry guide movement event results from either a command generated by the controller in response to a specified condition (e.g., automatically configuring the EGM for draping) or in response to a user command, (e.g., input received via any appropriate technique, including at one or more master input devices at the operator's console). Several alternative configurations of the first and second brakes of dual brake assembly 205 can be used in fifth state 405. In a first alternative, the first brake is disengaged, the second brake is engaged, and actuator commanded torque (torque supplied by the actuator in response to a command from controller 290) is used to hold second link 204 stationary (e.g., the actuator and the second brake work together to minimize vibration induced movement of entry guide manipulator 230). Alternately, the first brake is disengaged, the second brake is engaged, and actuator commanded torque is not used. In another alternative, both the first and second brakes are engaged, and actuator commanded torque is not used. In yet another alternative, if the first and second brakes are both joint brakes (e.g., neither brake is an actuator brake), both brakes are engaged and actuator commanded torque is used. (If the first brake is an actuator brake, then engaging the actuator brake while using actuator commanded torque is counterproductive because the actuator brake would fight the actuator commanded torque rather than adding to the actuator commanded torque.)

If while in fifth state 405, a power-off event or a fault event occurs, controller 290 transitions from fifth state 405 to first state 401. If the fault event is an actuator always active fault, controller 290 does not transition to first state 401, but instead transitions to a sixth state 406. If while in fifth state 405, an EGM movement complete event is received by controller 290, controller 290 transitions from fifth state 405 to second state 402.

As indicated above, if a joint actuator fails in an always active state, controller 290 detects an actuator always active fault and transitions to an optional sixth state 406. In sixth state 406, sometimes referred to as an actuator always active state 606, controller 290 engages the first brake and the second brake of dual brake assembly 205. The first brake brakes the actuator output, and the second brake holds the second link as described previously. If the power is not turned off to dual brake assembly 205 in such a case, this is a fault condition and the holding force on the joint is reduced so that dual brake assembly 205 can slip when the egress force is applied to second link 204. Thus, after a predetermined time, e.g., a time sufficient for the first brake to be engaged and stop the output of the actuator, controller 290 transitions from sixth state 406 to first state 401. Similarly, if power to joint assembly 203 is turned-off to stop the actuator, controller 290 transitions from sixth state 406 to first state 401. While it is not shown in FIG. 4A, if the actuator always active fault is cleared, e.g., controller 290 regains control of the actuator within the predetermined time, controller 290 transitions from sixth state 406 back to second state 402. If a joint is not powered, an actuator is not included in the joint, and so sixth state 406 would not be used by the controller.

Figure 4B:
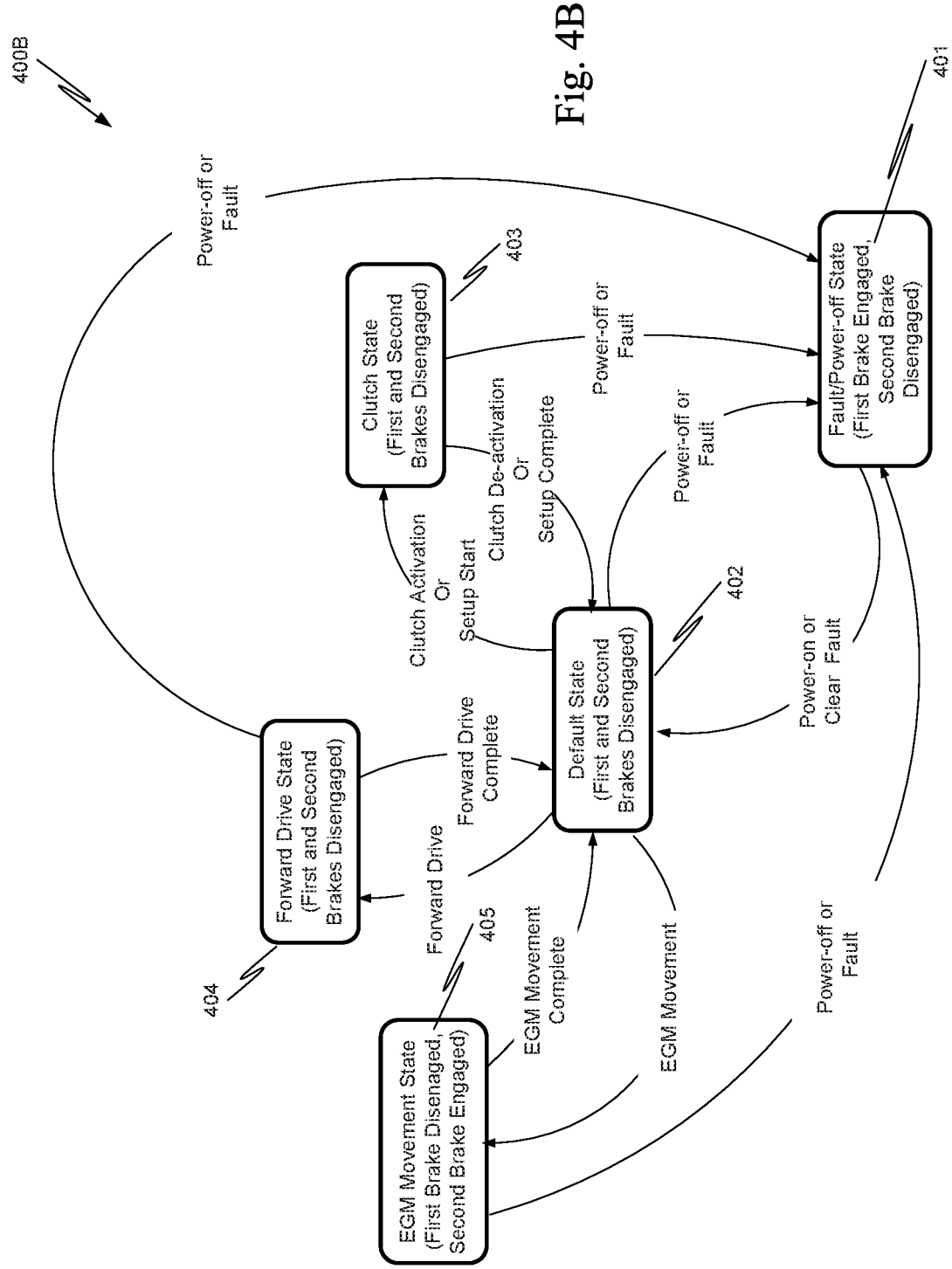
FIG. 4B is a second state diagram of a controller used to control the states of a dual brake assembly.

In another implementation illustrated in FIG. 4B, sixth state 406 is eliminated, and an actuator always active fault is processed the same as any other fault. The first brake in dual brake assembly 205 is sized to handle an always active actuator, the other states and transitions between states are the same as described with respect to FIG. 4A, and so that description is not repeated here, but instead is incorporated by reference.

Figure 5A:
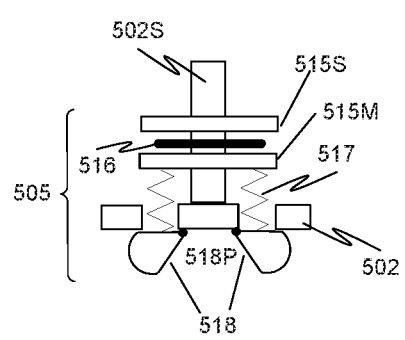
FIGS. 5A to 5C are illustrations of a dual brake assembly that is implemented using a single brake.
Figure 5B:
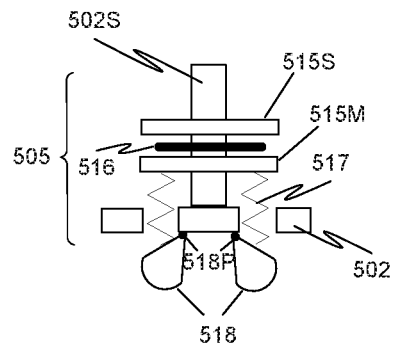
Figure 5C:
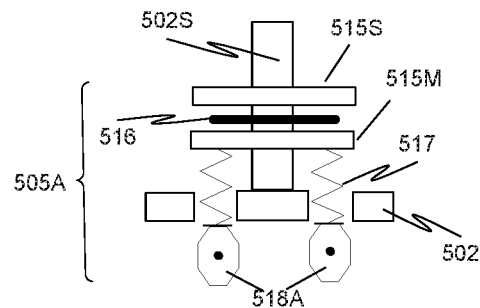

In the examples of FIGS. 3B to 3E, the dual brake assembly is implemented using two different brakes. In FIGS. 5A to 5C, the dual brake assembly has two portions with different brake holding strengths, but the two portions are implemented using a single actuator brake. Dual brake assembly 505 and dual brake assembly 505A are power-off brakes so that power is applied to disengage the brake.

Dual brake assembly 505 is mounted on an actuator 502. A brake rotor 516 is rotationally keyed to shaft 502S of actuator 502, and brake rotor 516 floats axially with respect to shaft 502S such that moving caliper 515M can push brake rotor 516 against stationary caliper 515S. Alternatively, if brake rotor 516 were also axially fixed to shaft 502S, only moving caliper 515M would bear on brake rotor 516, and so stationary caliper 515S may be eliminated. For the same forces and materials, this would cut the holding strength in half.

When power is off to dual brake assembly 505, a plurality of springs 517 forces moving caliper 515M against brake rotor 516 and towards stationary caliper 515S. Stationary caliper 515S is coupled to a housing of actuator 502. If power is applied to dual brake assembly 505, an electromagnetic overcomes the force on moving caliper 515M from plurality of springs 517, and pulls moving caliper 515M away from brake rotor 516 so that shaft 502S moves freely.

The holding strength of dual brake assembly 505 is proportional to the normal force that is applied to brake rotor 516 by calipers 515M, 515S. The normal force is supplied by plurality of springs 517 that push moving caliper 515M towards brake rotor 516. When dual brake assembly 505 is disengaged, the electromagnet creates a force in the opposite direction of the normal force supplied by plurality of spring 517 to pull moving caliper 515M away from brake rotor 516. The brake holding strength is changed by changing the normal force supplied by plurality of springs 517.

Changing the normal force supplied by plurality of springs 517 is achieved, in this aspect, by changing the displacement offset of plurality of springs 517. In dual brake assembly 505, each of plurality of springs 517 rests on a different one of a plurality of spring caps 518. Each spring cap rotates about a pivot point 518P. The angular position of each of plurality of spring caps 518 is controlled by a controller. The combination of plurality of springs 517 and plurality of spring caps 518 is one example of a variable load assembly. The variable load assembly is, in this aspect, a variable load spring assembly.

The controller can change the angular positon of each of plurality of spring caps 518 about its pivot point. Changing the angular position of a spring cap changes the displacement offset on the associated spring. As shown in FIG. 5A, each of plurality of spring caps 518 is in first position, and the length of each of plurality of springs 517 is restricted to the distance between a surface of the corresponding spring cap and a surface of moving caliper 515M. In FIG. 5B, each of plurality of spring caps 518 is in second position, and the length of each of plurality of springs 517 again is restricted to a different distance between the surface of the corresponding spring cap and the surface of moving caliper 515M. The length of the spring in FIG. 5B is longer than the length of the spring in FIG. 5A. Stated alternatively, each of plurality of springs 517 is compressed more in FIG. 5A than in FIG. 5B. Thus, plurality of springs 517 provides a larger normal force in FIG. 5A than in FIG. 5B, and so the holding strength of dual brake assembly 505 is greater for the configuration illustrated in FIG. 5A than for the configuration illustrated in FIG. 5B.

In another aspect, one of plurality of spring caps 518 is in the first position and a second of the plurality of spring caps 518 is in the second positon. With this configuration, a normal force between the normal force of FIG. 5A and the normal force of FIG. 5B is obtained.

An advantage of dual brake assembly 505 is that finer adjustments in the normal force can be achieved and so finer adjustments of the holding strength can be achieved relative to prior art single brake configurations. Depending on the angular position of plurality of spring caps 518, plurality of springs 517 would have different displacements and would create different normal forces. The spring force is generally linear with deflection or a change in airgap, while the force from am electromagnet is not. Therefore, a spring applied brake can be more easily be configured to apply a specific force or torque, and a spring applied brake is less susceptible to variation in holding strength due to tolerance stack-up in the various components which make up the brake assembly than an electromagnetically applied brake.

Dual brake assembly 505A is equivalent to dual brake assembly 505, except plurality of spring caps 518 has been replaced with a plurality of cam assemblies 518A. As each cam assembly rotates, the displacement of the spring resting on the same changes, and so the brake holding strength of dual brake assembly changes. The combination of plurality of springs 517 and plurality of cam assemblies 518A is another example of a variable load assembly.

FIG. 6 is a cut-away illustration of one implementation of joint assembly 203 with a dual brake assembly 605. Dual brake assembly 605 includes an actuator brake 605A and a joint brake 605B. Joint assembly 203 is mounted on first link 202 and allows second link 204 to be moved relative to first link 202.

Joint assembly 203 further includes an actuator, which is an electric motor, and a transmission assembly, which is harmonic drive 620. The electric motor includes motor stator windings 631, motor rotor magnets 633, a motor bearing 637, and a shaft 657.

Joint assembly 203 also includes a joint absolute position sensor 619, a motor position sensor 658, and joint bearings 601. In this aspect, joint bearings 601 are tapered roller bearings.

Joint brake 605B includes an electromagnetic coil 699 and a moving armature 610. A flexure 611 connects armature 610 to hub 612. Hub 612 is fixed to second link 204.

Actuator brake 605A is a motor brake 605A that brakes the electric motor comprising the actuator of joint assembly 203. Motor brake 605A includes an electromagnet coil 640, a moving caliper 645, a stationary caliper 646, and a brake rotor 644. Brake rotor 644 is keyed to motor shaft 657. Springs that push on moving caliper 645 to sandwich brake rotor 644 between the two calipers when no power is applied are not visible in FIG. 6.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that include, or do not include, surgical aspects.

In some of the above examples, the terms "proximal" or "proximally" are used in a general way to describe an object or element which is closer to a manipulator arm base along a kinematic chain of system movement or farther away from a remote center of motion (or a surgical site) along the kinematic chain of system movement. Similarly, the terms "distal" or "distally" are used in a general way to describe an object or element which is farther away from the manipulator arm base along the kinematic chain of system movement or closer to the remote center of motion (or a surgical site) along the kinematic chain of system movement.

As used herein, "first," "second," "third," "fourth," etc. are adjectives used to distinguish between different components or elements. Thus, "first," "second," "third," "fourth," etc. are not intended to imply any ordering of the components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

The various controllers described herein can be implemented by software executing on a processor, hardware, firmware, or any combination of the three. When the controllers are implemented as software executing on a processor, the software is stored in a memory as computer readable instructions and the computer readable instructions are executed on the processor. All or part of the memory can be in a different physical location than a processor so long as the processor can be coupled to the memory. Memory refers to a volatile memory, a non-volatile memory, or any combination of the two.

Also, the functions of the various controllers, as described herein, may be performed by one unit, or divided up among different components, each of which may be implemented in turn by any combination of hardware, software that is executed on a processor, and firmware. When divided up among different components, the components may be centralized in one location or distributed across the system for distributed processing purposes. The execution of the various controllers results in methods that perform the processes described above for the various controllers.

A processor is coupled to a memory containing instructions executed by the processor. This could be accomplished within a computer system, or alternatively via a connection to another computer via modems and analog lines, or digital interfaces and a digital carrier line, or via connections using any of the protocols described above. In view of this disclosure, instructions used in any part of or all of the processes described herein can be implemented in a wide variety of computer system configurations using an operating system and computer programming language of interest to the user.

Herein, a computer program product comprises a computer readable medium configured to store computer readable code needed for any part of or all of the processes described herein, or in which computer readable code for any part of or all of those processes is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a tangible computer readable medium configured to store computer readable instructions for any part of or all of the processes or in which computer readable instructions for any part of or all of the processes is stored. Non-transitory tangible computer program products are CD-ROM discs, DVD discs, flash memory, ROM cards, floppy discs, magnetic tapes, computer hard drives, and other physical storage mediums.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A system comprising:
a first link having a first end portion and a second end portion;
a second link having a first end portion and a second end portion;
a joint connected to the second end portion of the first link and to the first end portion of the second link;
a dual brake assembly coupled to the first link and to the second link, wherein the dual brake assembly includes a first brake and a second brake, wherein braking the dual brake assembly reduces relative motion between the first and second links, wherein the first brake provides a first brake holding strength when physically engaged, wherein the second brake provides a second brake holding strength when physically engaged, and wherein the second brake holding strength is different from the first brake holding strength; and
a controller, wherein: in response to a clutch activation being commanded, the controller issues a command that causes the dual brake assembly to transition to a clutch state in which the first brake is physically disengaged and the second brake is physically disengaged, and in response to the clutch activation being dropped subsequent to the clutch activation being commanded, the controller causes the dual brake assembly to transition from the clutch state to a first state in which the first brake and the second brake are physically disengaged.

2. The system of claim 1, wherein:
the first brake is physically engaged when unpowered; and
the second brake is physically disengaged when unpowered.

3. The system of claim 1, wherein:
the first brake comprises an actuator brake; and
the second brake comprises a joint brake.

4. The system of claim 1, wherein: in response to the system being in a fault state, the controller causes the first brake to be physically engaged and the second brake to be physically disengaged.

5. The system of claim 1, wherein during a procedure performed using the system, the controller causes the first brake to be physically disengaged and the second brake to be physically engaged.

6. The system of claim 1, further comprising:
an actuator coupled to the joint, wherein activation of the actuator causes the joint to move the second link relative to the first link; and
the controller configured to cause the first brake to be physically engaged and the second brake to be physically engaged to restrict movement of the second link relative to the first link upon failure of the actuator in a state configured to cause movement of the second link relative to the first link.

7. The system of claim 1, wherein:
the first brake comprises a housing;
the second brake comprises a housing;
the housing of the first brake is mounted on the first link and the first brake is coupled to the second link to brake the second link; and
the housing of the second brake is mounted on the first link and the second brake is coupled to the second link to brake the second link.

8. The system of claim 1, further comprising:
an actuator mounted on the first link; and
a transmission assembly coupled to the actuator and to the second link;
wherein:
the first brake is coupled to the actuator; and
the second brake is mounted on the first link and is coupled to the second link.

9. The system of claim 1, further comprising:
a transmission assembly mounted on the first link and coupled to the second link; and
an actuator connected to the transmission assembly;
wherein:
the first brake is coupled to the actuator; and
the second brake is mounted on the first link and is coupled to the second link.

10. The system of claim 1, the controller being configured to:
  physically disengage the first brake and physically disengage the second brake to allow free movement of the second link relative to the first link; and
  physically engage the first brake and physically disengage the second brake to restrict movement of the second link relative to the first link.

11. The system of claim 10, the controller being further configured to:
  physically disengage the first brake and physically engage the second brake during a procedure performed using the system; and
  physically engage the first brake and physically engage the second brake to restrict movement of the second link relative to the first link upon failure of an actuator in a state configured to cause movement of the second link relative to the first link.

12. A method of controlling motion of a second link relative to a first link in a system comprising a dual brake assembly coupled to the first link and to the second link, wherein the dual brake assembly includes a first brake and a second brake, the method comprising:
  causing at least one brake to be physically engaged to restrict movement of the second link relative to the first link, wherein the at least one brake is selected from the group consisting of: the first brake and the second brake, wherein the first brake provides a first brake holding strength when physically engaged, wherein the second brake provides a second brake holding strength when physically engaged, and wherein the second brake holding strength is different from the first brake holding strength; and
  in response to a clutch activation being commanded, issuing a command that causes the dual brake assembly to transition to a clutch state in which the first brake is physically disengaged and the second brake is physically disengaged, and in response to the clutch activation being dropped subsequent to the clutch activation being commanded, causing the dual brake assembly to transition from the clutch state to a first state in which the first brake and the second brake are physically disengaged.

13. The method of claim 12, further comprising:
  physically disengaging the first brake and physically engaging the second brake during a procedure performed using the system; and
  physically engaging the first brake and physically engaging the second brake to restrict movement of the second link relative to the first link upon failure of an actuator in a state configured to cause movement of the second link relative to the first link.

14. The method of claim 12, further comprising:
  when the system enters a powered off state, physically engaging the first brake and physically disengaging the second brake.

15. A computer-aided medical system comprising:
  a patient side support system comprising:
    a first link having a first end portion and a second end portion;
    a second link having a first end portion and a second end portion;
    a joint assembly connected to the second end portion of the first link and to the first end portion of the second link, the joint assembly comprising:
      an actuator configured to cause the joint assembly to move the second link relative to the first link; and
      a dual brake assembly coupled to the first link, to the second link, and to the actuator, wherein the dual brake assembly includes a first brake and a second brake, wherein the first brake provides a first brake holding strength when physically engaged, wherein the second brake provides a second brake holding strength when physically engaged, and wherein the second brake holding strength is different from the first brake holding strength; and
    a controller coupled to the actuator and to the dual brake assembly, wherein the controller is configured to command the dual brake assembly, wherein: in response to a clutch activation being commanded, the controller issues a command that causes the dual brake assembly to transition to a clutch state in which the first brake is physically disengaged and the second brake is physically disengaged, and in response to the clutch activation being dropped subsequent to the clutch activation being commanded, the controller causes the dual brake assembly to transition from the clutch state to a first state in which the first brake and the second brake are physically disengaged.

16. The computer-aided medical system of claim 15, wherein:
  the first brake is physically engaged when unpowered; and
  the second brake is physically engaged when powered.

17. The computer-aided medical system of claim 16, wherein the controller is configured to command the dual brake assembly by:
  in response to the computer-aided medical system being in a fault state, commanding the first brake to be physically engaged and to command the second brake to be physically disengaged; or
  commanding, during a procedure performed using the computer-aided medical system, the first brake to be physically disengaged and to command the second brake to be physically engaged.

18. The computer-aided medical system of claim 15, wherein if the computer-aided medical system is in a power off state, the first brake is unpowered and physically engaged and the second brake is unpowered and physically disengaged.

* * * * *